United States Patent [19]

Bryan et al.

[11] Patent Number: 6,050,955

[45] Date of Patent: Apr. 18, 2000

[54] BIOPSY APPARATUS AND METHOD

[75] Inventors: Graham W. Bryan, Norwalk; Paul A. Matula, Brookfield, both of Conn.

[73] Assignee: United States Surgical Corporation, Norwalk, Conn.

[21] Appl. No.: 09/157,120

[22] Filed: Sep. 18, 1998

Related U.S. Application Data

[60] Provisional application No. 60/059,547, Sep. 19, 1997.

[51] Int. Cl.⁷ .................................................. A61B 10/00
[52] U.S. Cl. .......................... 600/566; 600/564; 600/567; 606/167
[58] Field of Search .................................... 600/562, 564, 600/565, 566, 567, 568; 604/22; 606/130, 167, 170, 181, 184, 185

[56] References Cited

U.S. PATENT DOCUMENTS

| Re. 33,258 | 7/1990 | Onik et al. ................................. 604/22 |
| Re. 34,056 | 9/1992 | Lindgren et al. ........................ 128/754 |
| 737,293 | 8/1903 | Summerfeldt ........................... 606/159 |
| 1,585,934 | 5/1926 | Muir ......................................... 600/567 |
| 1,663,761 | 3/1928 | Johnson ................................... 606/159 |

(List continued on next page.)

FOREIGN PATENT DOCUMENTS

| 0 010 321 A1 | 4/1980 | European Pat. Off. . |
| 0 019 104 | 11/1980 | European Pat. Off. . |
| 0 207 726 A2 | 1/1987 | European Pat. Off. . |
| 0 238 461 A1 | 9/1987 | European Pat. Off. . |
| 0 378 692 | 7/1990 | European Pat. Off. . |

(List continued on next page.)

OTHER PUBLICATIONS

Automatic Soft Tissue Biopsy System, (ASAP™) Operational Guidelines, Microvasive Boston Scientific Corp., (2 pgs.).

When It Comes To Core Samples, I Demand Accuracy And Consistency For All My Patients, The Bard Biopty Biopsy System, Bard® Radiology, (4 pgs.).

Nucleotome® System Automated Percutaneous Lumbar Disectomy™, *Surgical Dynamics*,®(3 pgs.).

Introducing The Singular Technology For Multi–Core Microcalification Sampling, *Biopsy Medical Inc.*, (2 pgs.).

Mammotome Multi–Probe, Probe And Motorized Driver, Instructions for Use, *Biopsy Medical Inc.*, (3 pgs.).

Stereotaxic Needle Core Biopsy of Breast Lesions Using A Regular Mammographic Table With An Adaptable Stereotaxic Device, Caines et al., pp. 317–321, Aug. 1993.

Stereotactic Breast Biopsy with a Biopsy Gun, Parker, MD et al., pp. 741–747, Sep. 1990.

Stereotactic Percutaneous Breast Core Biopsy Technical Adaptation And Initial Experience, Lovin, MD et al., pp. 135–143, 1990.

(List continued on next page.)

*Primary Examiner*—Cary O'Connor
*Assistant Examiner*—Charles Marmor, II

[57] ABSTRACT

An apparatus and method for the biopsy of tissue specimens and, more particularly, a single insertion multiple sample percutaneous biopsy apparatus and method are provided. A tip at a distal end of a vacuum support tube is introduced into a tissue mass. The vacuum support tube is retracted exposing a basket tube bounded by a front washer and a rear washer mounted thereabout forming a tissue basket. The basket tube is supported internally by a thrust tube which provides structure to the apparatus to allow it to penetrate tissue. The thrust tube and the basket tube are in fluid communication and are provided with suction to draw tissue inward. The tissue is then severed by rotating and advancing a knife edge at the distal end of the vacuum support tube. The tissue basket is withdrawn and the tissue sample is removed by rotating the vacuum support tube. The tissue sample is sliced longitudinally, and a stripper scrapes the tissue sample from an opening in the vacuum support tube.

19 Claims, 14 Drawing Sheets

U.S. PATENT DOCUMENTS

| | | | |
|---|---|---|---|
| 1,867,624 | 7/1932 | Hoffman | 600/567 |
| 2,729,210 | 1/1956 | Spencer | 128/2 |
| 3,400,708 | 9/1968 | Scheidt | 128/2 |
| 3,477,423 | 11/1969 | Griffith | 128/2 |
| 3,561,429 | 2/1971 | Jewett et al. | 128/2 |
| 3,590,808 | 7/1971 | Muller | 128/2 B |
| 3,606,878 | 9/1971 | Kellogg, Jr. | 128/2 B |
| 3,732,858 | 5/1973 | Banko | 128/2 B |
| 3,734,099 | 5/1973 | Bender et al. | 128/305 |
| 3,844,272 | 10/1974 | Banko | 128/2 B |
| 3,929,123 | 12/1975 | Jamshidi | 128/2 B |
| 3,989,033 | 11/1976 | Halpern | 128/2 B |
| 3,995,619 | 12/1976 | Glatzer | 128/2 B |
| 4,099,518 | 7/1978 | Baylis et al. | 128/2 B |
| 4,200,106 | 4/1980 | Douvas et al. | 128/305 |
| 4,203,444 | 5/1980 | Bonnell et al. | 128/276 |
| 4,210,146 | 7/1980 | Banko | 128/305 |
| 4,340,066 | 7/1982 | Shah | 128/749 |
| 4,396,021 | 8/1983 | Baumgartner | 128/754 |
| 4,600,014 | 7/1986 | Beraha | 128/754 |
| 4,644,951 | 2/1987 | Bays | 128/305 |
| 4,651,753 | 3/1987 | Lifton | 128/751 |
| 4,660,267 | 4/1987 | Wheeler | 29/437 |
| 4,662,869 | 5/1987 | Wright | 604/22 |
| 4,674,502 | 6/1987 | Imonti | 128/305 |
| 4,681,123 | 7/1987 | Valtchev | 128/753 |
| 4,699,154 | 10/1987 | Lindgren | 128/754 |
| 4,702,260 | 10/1987 | Wang | 128/753 |
| 4,702,261 | 10/1987 | Cornell et al. | 128/754 |
| 4,708,147 | 11/1987 | Haaga | 128/753 |
| 4,711,250 | 12/1987 | Gilbaugh, Jr. et al. | 128/765 |
| 4,733,671 | 3/1988 | Mehl | 128/754 |
| 4,735,215 | 4/1988 | Goto et al. | 128/754 |
| 4,776,346 | 10/1988 | Beraha et al. | 128/754 |
| 4,781,202 | 11/1988 | Janese | 128/754 |
| 4,799,494 | 1/1989 | Wang | 128/753 |
| 4,838,280 | 6/1989 | Haaga | 128/751 |
| 4,844,088 | 7/1989 | Kambin | 128/753 |
| 4,874,375 | 10/1989 | Ellison | 604/164 |
| 4,881,551 | 11/1989 | Taylor | 128/754 |
| 4,907,598 | 3/1990 | Bauer | 128/753 |
| 4,907,599 | 3/1990 | Taylor | 128/754 |
| 4,917,100 | 4/1990 | Nottke | 128/749 |
| 4,924,878 | 5/1990 | Nottke | 128/751 |
| 4,936,835 | 6/1990 | Haaga | 604/265 |
| 4,940,061 | 7/1990 | Terwilliger et al. | 128/754 |
| 4,944,308 | 7/1990 | Akerfeldt | 128/754 |
| 4,953,558 | 9/1990 | Akerfeldt | 128/751 |
| 4,958,625 | 9/1990 | Bates et al. | 128/754 |
| 4,976,269 | 12/1990 | Mehl | 128/754 |
| 4,989,614 | 2/1991 | Dejter, Jr. et al. | 128/752 |
| 4,991,592 | 2/1991 | Christ | 128/754 |
| 5,031,634 | 7/1991 | Simon | 128/754 |
| 5,036,860 | 8/1991 | Leigh et al. | 128/754 |
| 5,047,008 | 9/1991 | de Juan, Jr. et al. | 604/22 |
| 5,048,538 | 9/1991 | Terwilliger | 128/754 |
| 5,080,655 | 1/1992 | Haaga | 604/265 |
| 5,106,364 | 4/1992 | Hayafuji et al. | 604/22 |
| 5,121,751 | 6/1992 | Panalletta | 128/754 |
| 5,127,419 | 7/1992 | Kaldany | 128/754 |
| 5,146,921 | 9/1992 | Terwilliger et al. | 128/754 |
| 5,183,052 | 2/1993 | Terwilliger et al. | 128/753 |
| 5,183,054 | 2/1993 | Burkholder et al. | 128/754 |
| 5,188,118 | 2/1993 | Terwilliger | 128/753 |
| 5,195,533 | 3/1993 | Chin et al. | 128/754 |
| 5,195,988 | 3/1993 | Haaga | 604/265 |
| 5,199,441 | 4/1993 | Hogle | 128/754 |
| 5,213,110 | 5/1993 | Kedem et al. | 128/754 |
| 5,220,926 | 6/1993 | Jones | 128/754 |
| 5,224,488 | 7/1993 | Neuffer | 128/751 |
| 5,226,909 | 7/1993 | Evans et al. | 606/159 |
| 5,226,910 | 7/1993 | Kajiyama et al. | 606/171 |
| 5,243,994 | 9/1993 | Ranalletta | 525/92 |
| 5,249,582 | 10/1993 | Taylor | 128/754 |
| 5,249,583 | 10/1993 | Mallaby | 128/754 |
| 5,254,105 | 10/1993 | Haaga | 604/265 |
| 5,273,051 | 12/1993 | Wilk | 128/751 |
| 5,282,476 | 2/1994 | Terwilliger | 128/753 |
| 5,284,156 | 2/1994 | Schramm et al. | 128/754 |
| 5,285,795 | 2/1994 | Ryan et al. | 128/750 |
| 5,290,303 | 3/1994 | Pingleton et al. | 606/170 |
| 5,301,684 | 4/1994 | Ogirala | 128/754 |
| 5,313,958 | 5/1994 | Bauer | 128/754 |
| 5,316,013 | 5/1994 | Striebel, II et al. | 128/754 |
| 5,320,110 | 6/1994 | Wang | 128/753 |
| 5,368,045 | 11/1994 | Clement et al. | 128/754 |
| 5,415,182 | 5/1995 | Chin et al. | 128/754 |
| 5,425,376 | 6/1995 | Banys et al. | 128/753 |
| 5,458,112 | 10/1995 | Weaver | 128/753 |
| 5,476,101 | 12/1995 | Schramm et al. | 128/754 |
| 5,477,862 | 12/1995 | Haaga | 128/754 |
| 5,492,130 | 2/1996 | Chiou | 128/753 |
| 5,505,211 | 4/1996 | Ohto et al. | 128/754 |
| 5,511,556 | 4/1996 | DeSantis | 128/754 |
| 5,526,822 | 6/1996 | Burbank et al. | 128/754 |
| 5,535,755 | 7/1996 | Heske | 128/754 |
| 5,546,957 | 8/1996 | Heske | 128/754 |
| 5,560,373 | 10/1996 | De Santis | 128/753 |
| 5,649,547 | 7/1997 | Richart et al. | 128/754 |
| 5,655,542 | 8/1997 | Weilandt | 128/754 |
| 5,660,186 | 8/1997 | Bachir | 600/567 |
| 5,687,739 | 11/1997 | McPherson et al. | 600/567 |
| 5,752,923 | 5/1998 | Terwilliger | 600/562 |
| 5,769,086 | 6/1998 | Ritchart et al. | 128/753 |
| 5,775,333 | 7/1998 | Burbank et al. | 128/754 |
| 5,779,647 | 7/1998 | Chau et al. | 600/564 |
| 5,794,626 | 8/1998 | Kieturakis | 600/567 |
| 5,810,857 | 9/1998 | Mackool | 606/167 |
| 5,817,033 | 10/1998 | DeSantis et al. | 600/562 |
| 5,879,357 | 3/1999 | Heaton et al. | 600/567 |
| 5,944,673 | 8/1999 | Gregoire et al. | 600/567 |

FOREIGN PATENT DOCUMENTS

| | | | |
|---|---|---|---|
| 0 442 851 A1 | 8/1991 | European Pat. Off. | |
| 0 536 888 A1 | 4/1993 | European Pat. Off. | |
| 0 561 732 A1 | 9/1993 | European Pat. Off. | |
| 1 161 400 | 8/1958 | France | |
| 1 267 960 | 6/1960 | France | |
| 2 332 743 | 6/1977 | France | |
| 2 654 609 | 5/1991 | France | |
| 935625 | 11/1955 | Germany | |
| 1 817 555 | 1/1971 | Germany | |
| 27 19 959 A1 | 11/1978 | Germany | |
| 159 394 | 3/1983 | Germany | |
| 42 16 694 A1 | 12/1992 | Germany | |
| 400319 | 2/1974 | U.S.S.R. | |
| 520 976 | 7/1976 | U.S.S.R. | |
| 648 219 | 2/1979 | U.S.S.R. | |
| 707 576 | 1/1980 | U.S.S.R. | |
| 0728 852 | 5/1980 | U.S.S.R. | |
| 1178422 | 9/1985 | U.S.S.R. | |
| 1192 795 | 11/1985 | U.S.S.R. | |
| 1454-419-A1 | 1/1989 | U.S.S.R. | 600/567 |
| 1641-297- A1 | 4/1991 | U.S.S.R. | 600/565 |
| 1 255 330 | 12/1971 | United Kingdom | |

| | | |
|---|---|---|
| 1 393 068 | 5/1975 | United Kingdom . |
| 2 237 992 | 5/1991 | United Kingdom . |
| WO 91/01112 | 2/1991 | WIPO . |
| WO 92/00040 | 1/1992 | WIPO . |
| WO 92/19159 | 11/1992 | WIPO . |
| WO 93/12707 | 7/1993 | WIPO . |
| WO 93/14707 | 8/1993 | WIPO . |
| WO 83/03343 | 10/1993 | WIPO . |
| WO 93/20753 | 10/1993 | WIPO . |
| WO 94/08512 | 4/1994 | WIPO . |
| WO 94/2172 | 11/1994 | WIPO . |
| WO 88/07839 | 10/1998 | WIPO . |

OTHER PUBLICATIONS

Selective Use of Image–Guided Large–Core Needle Biopsy of The Breast: Accuracy and Cost–Effectiveness, Doyle et al., pp. 281–284, Aug. 1995.

Breast Biopsy: A Comparative Study of Stereotaxially Guided Core and Excisional Techniques, Gisvold et al., pp. 815–820, Apr. 1994.

Stereotactic Core Needle Biopsy of Mammographic Breast Lesions as a Viable Alternative to Surgical iopsy, Mikhail, MD et al., pp. 363–367, 1994.

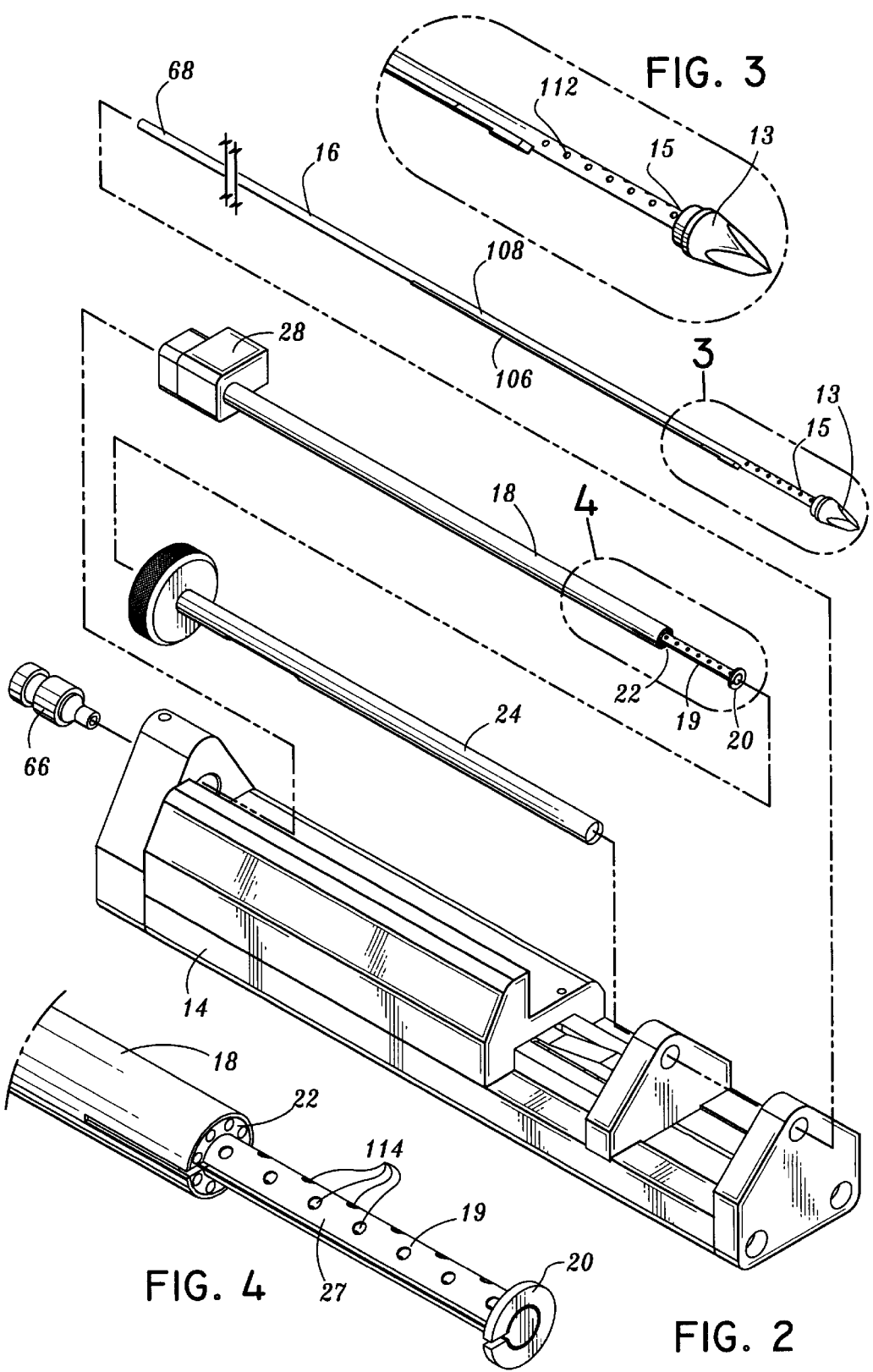

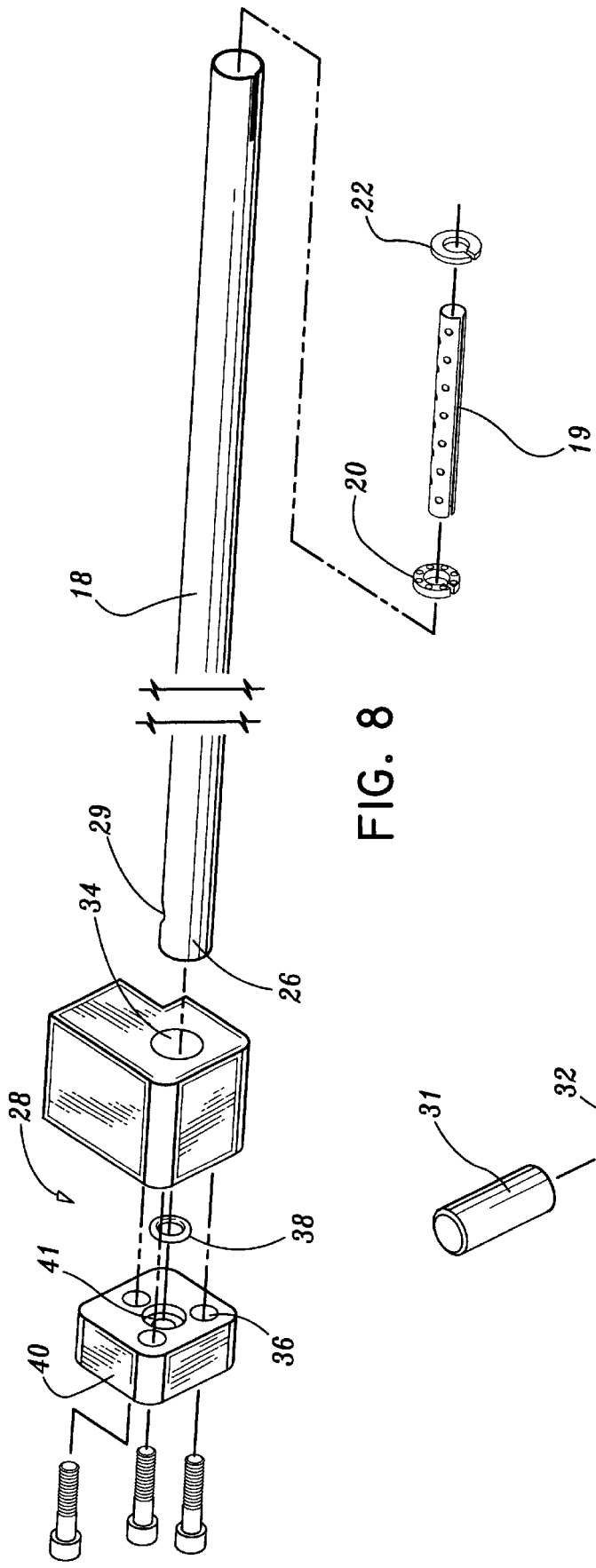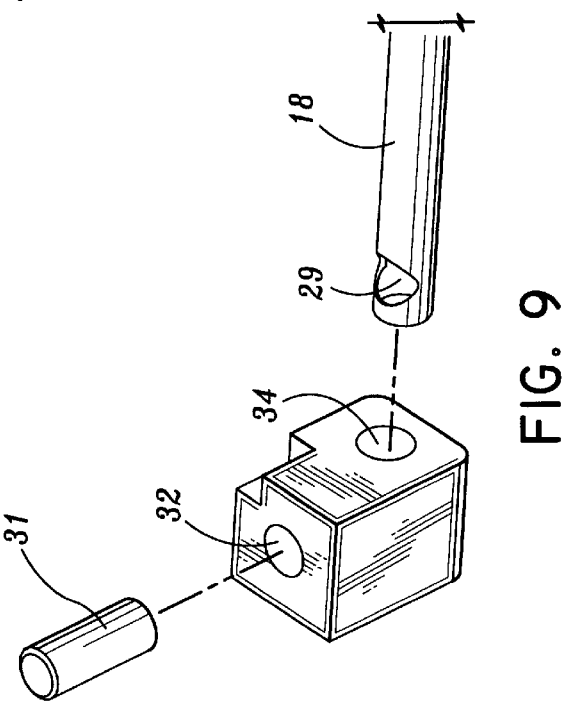

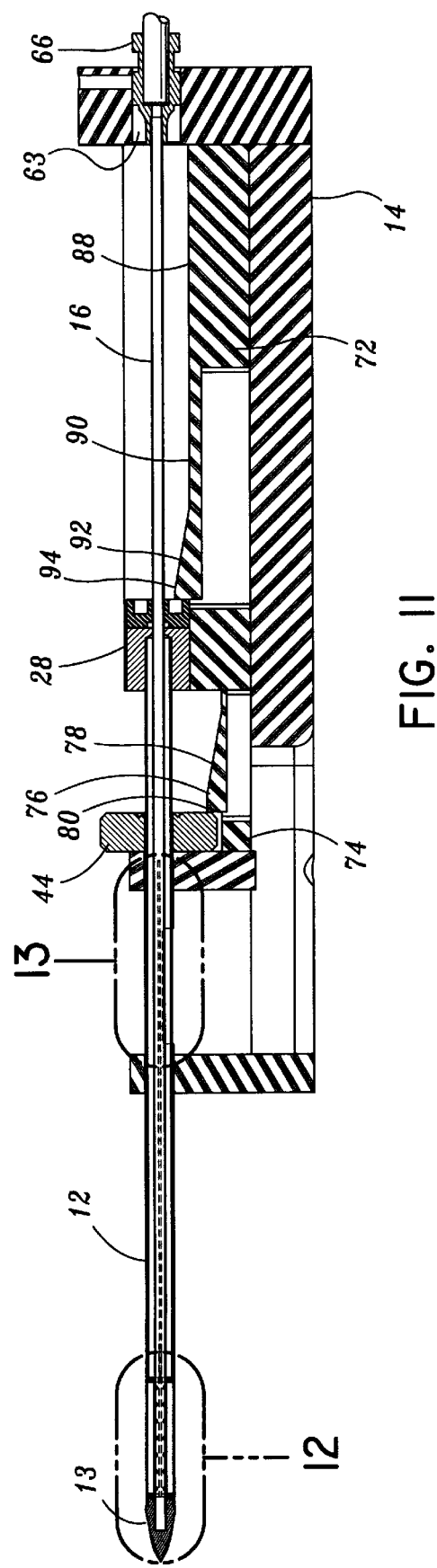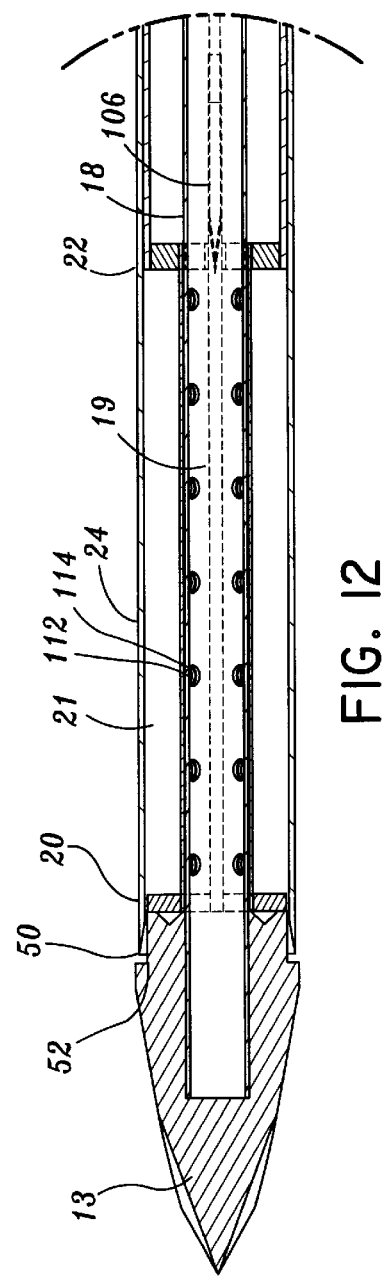
FIG. 11
FIG. 12

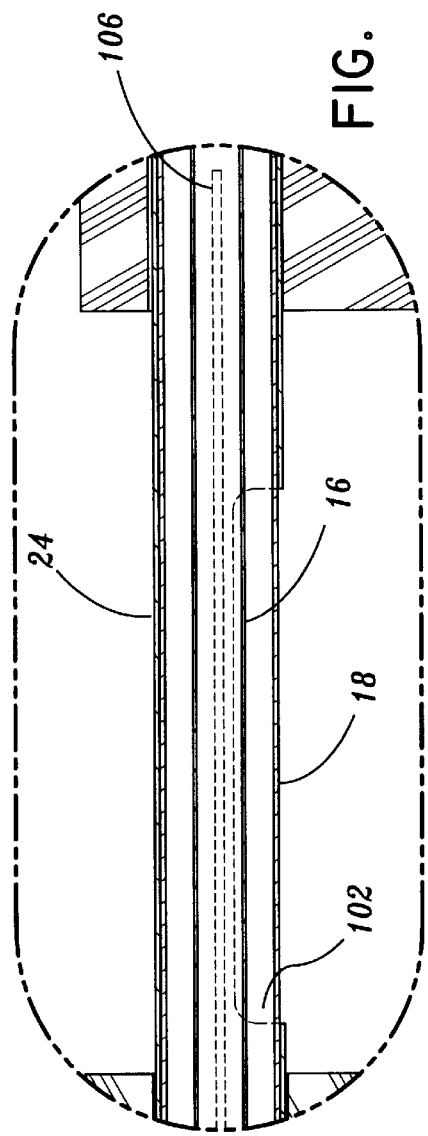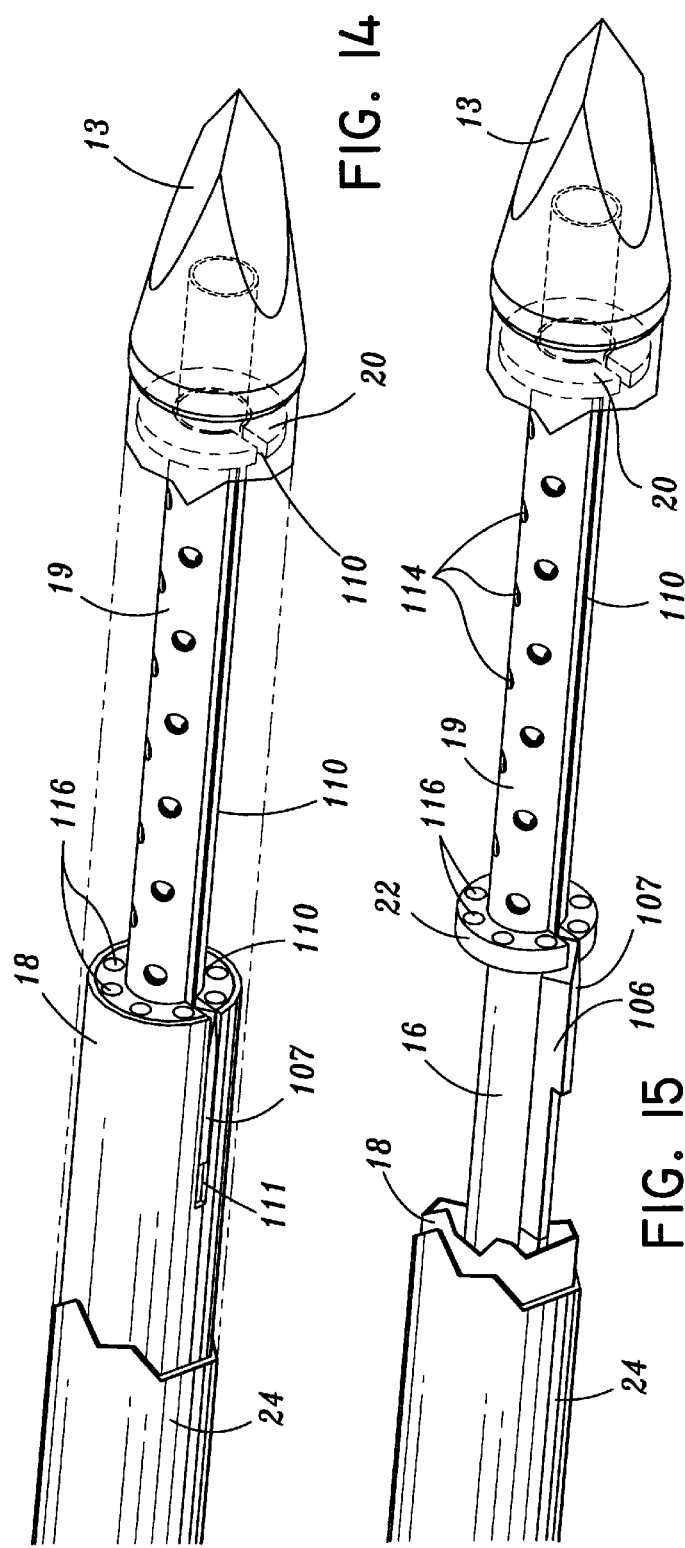

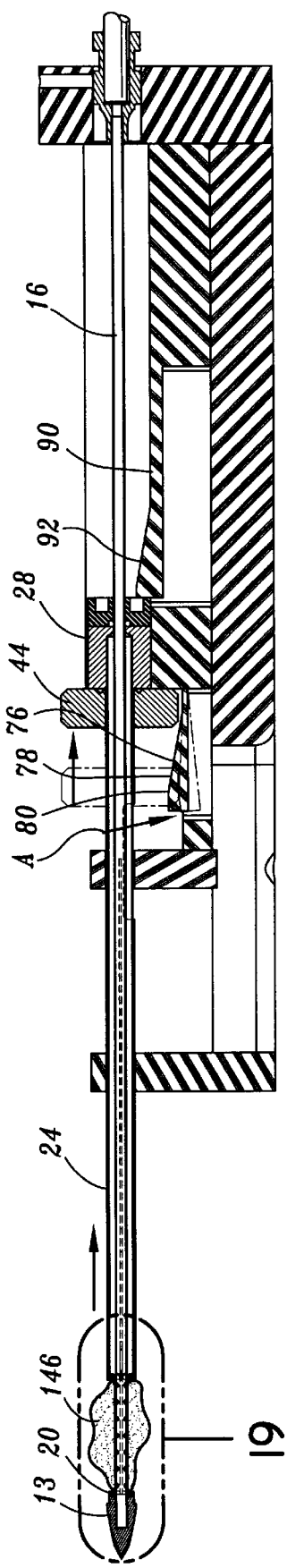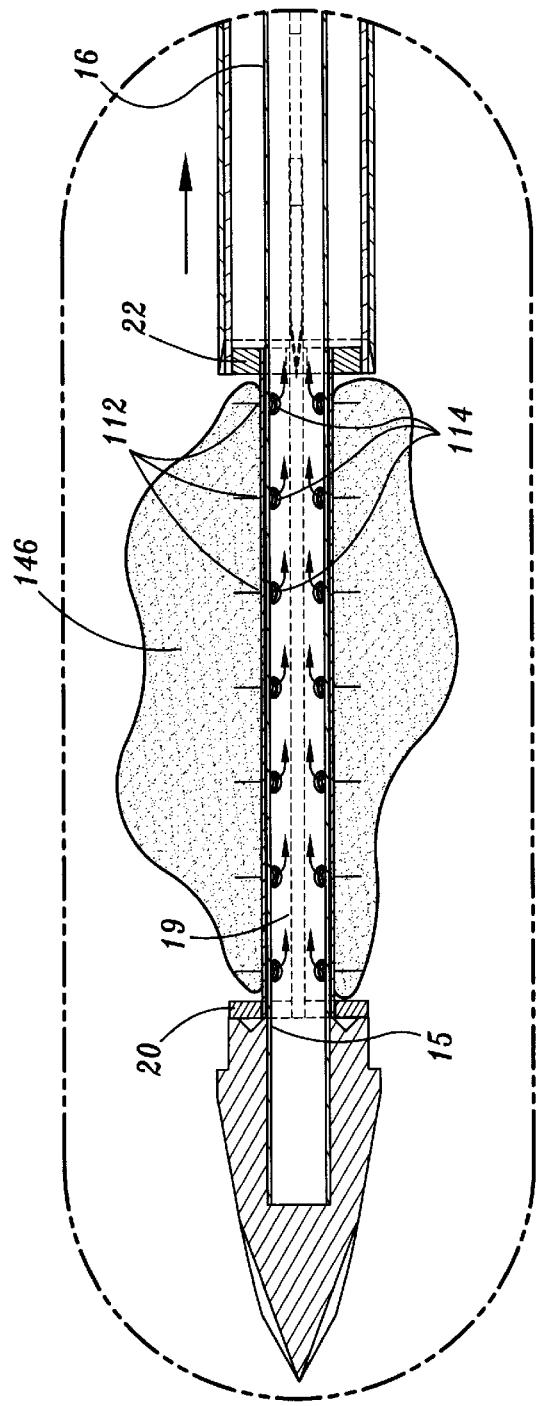

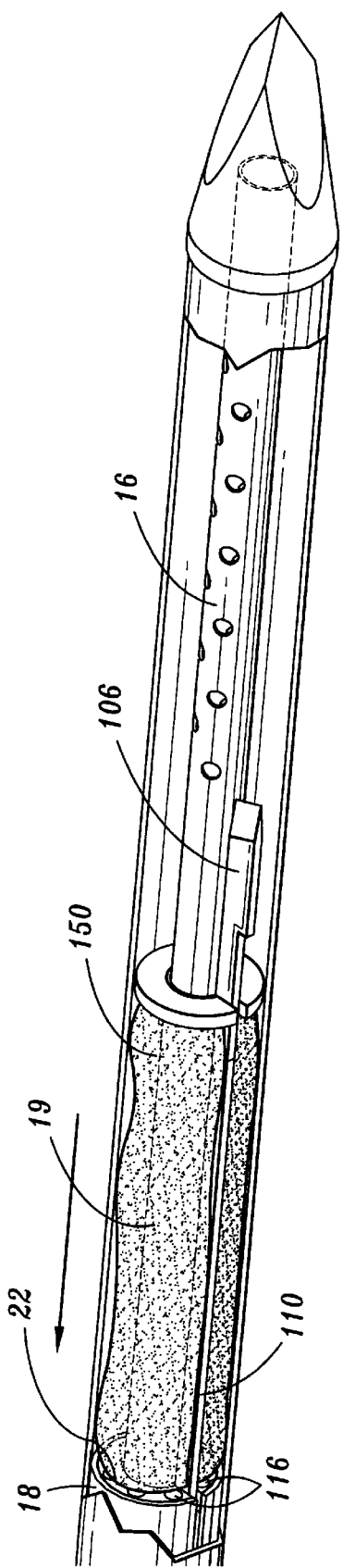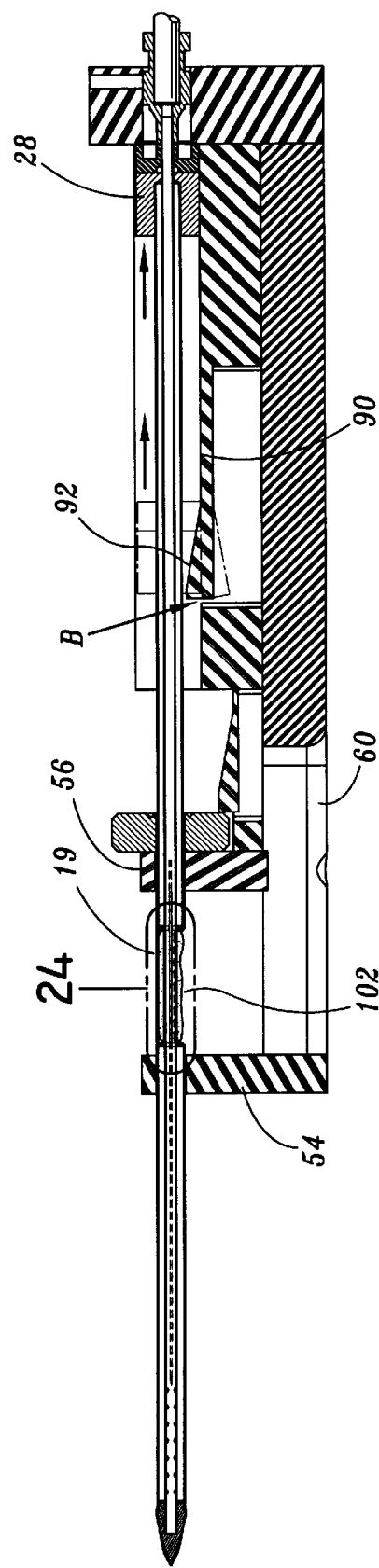

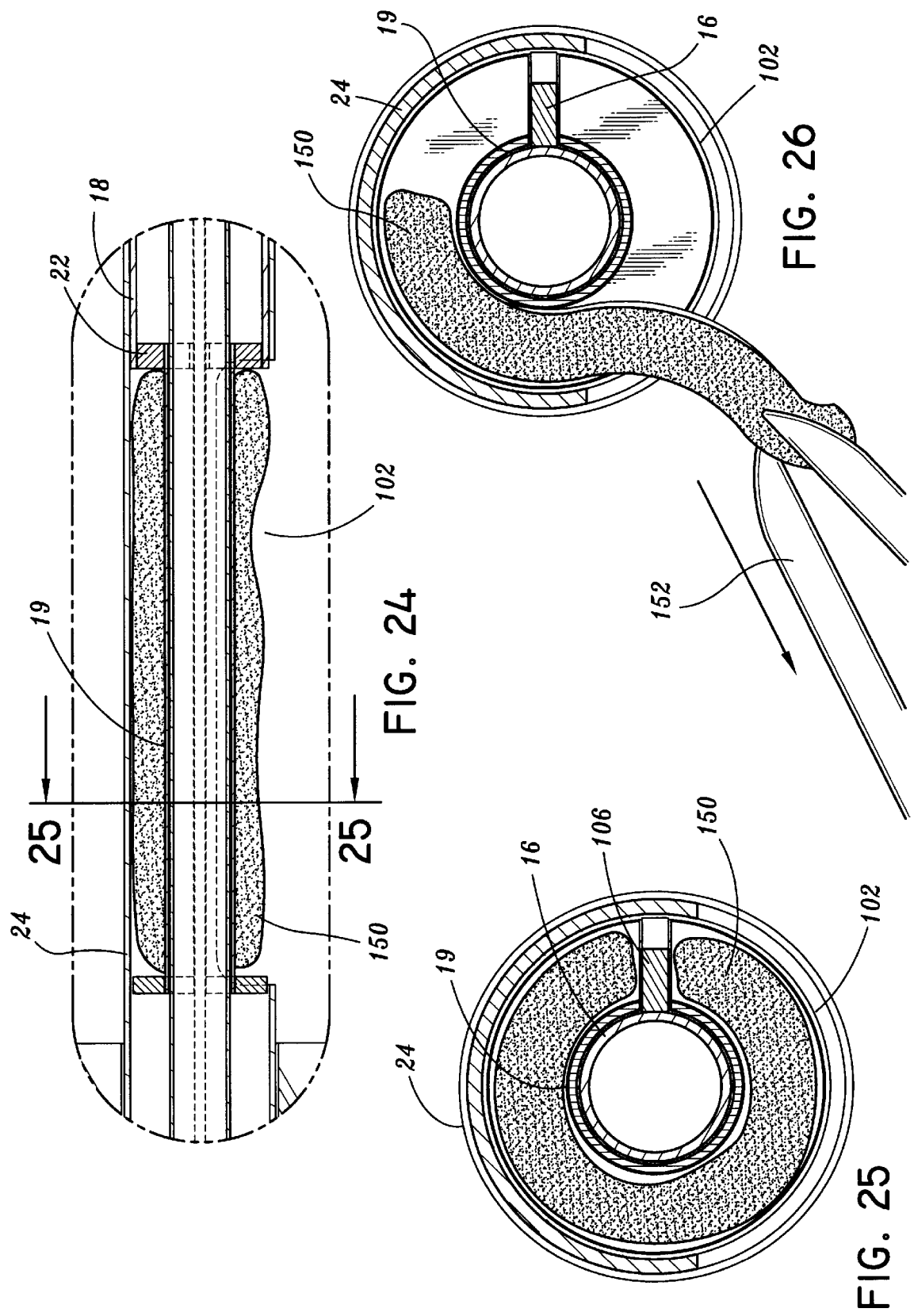

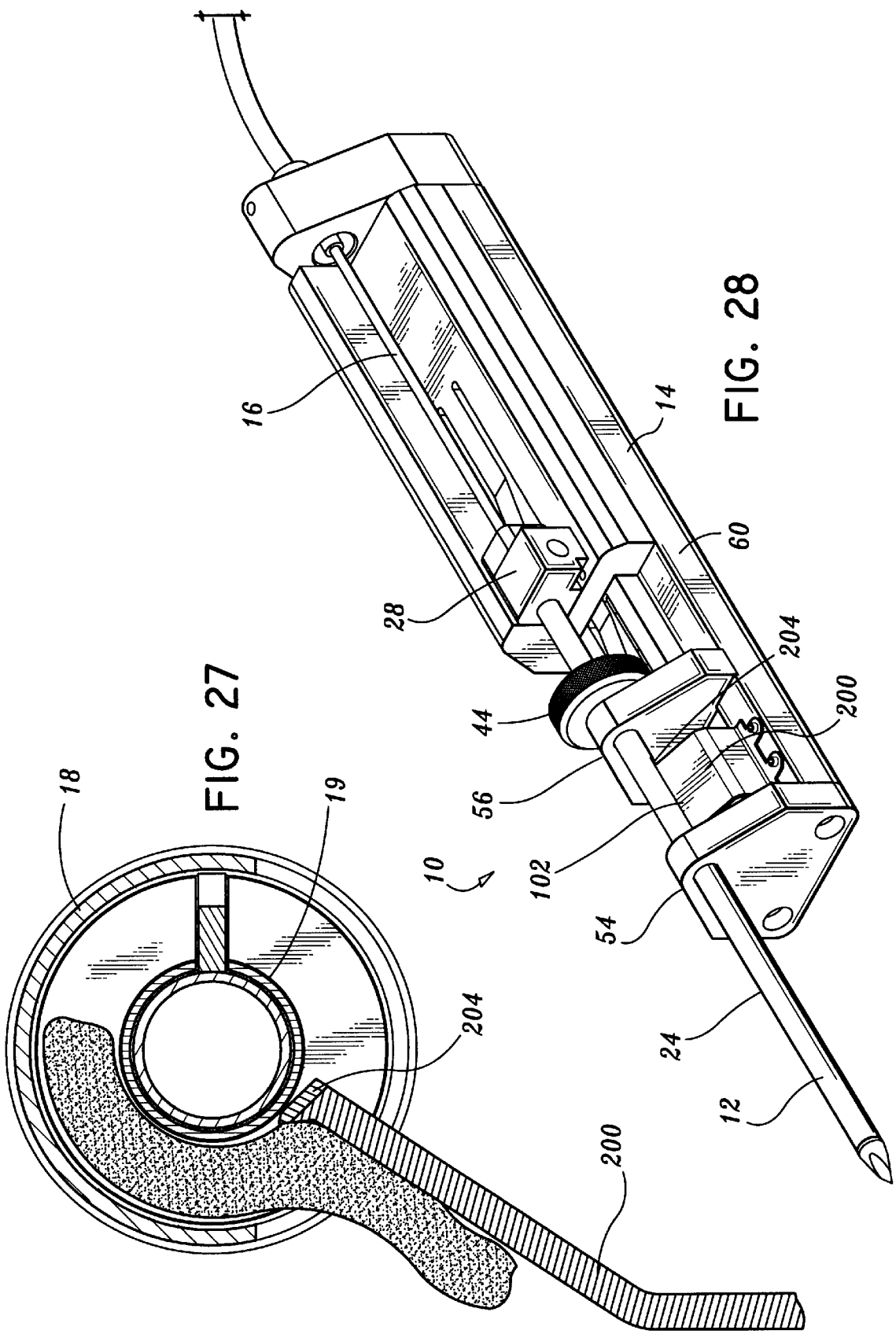

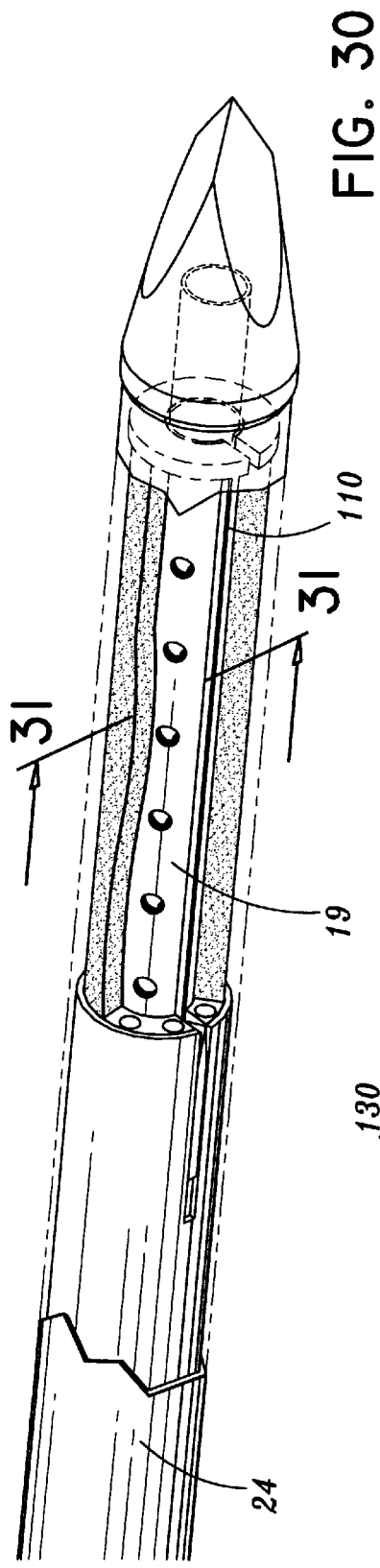
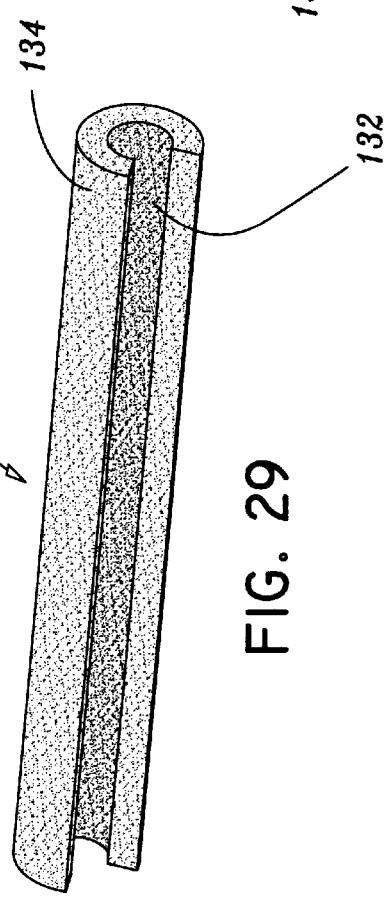
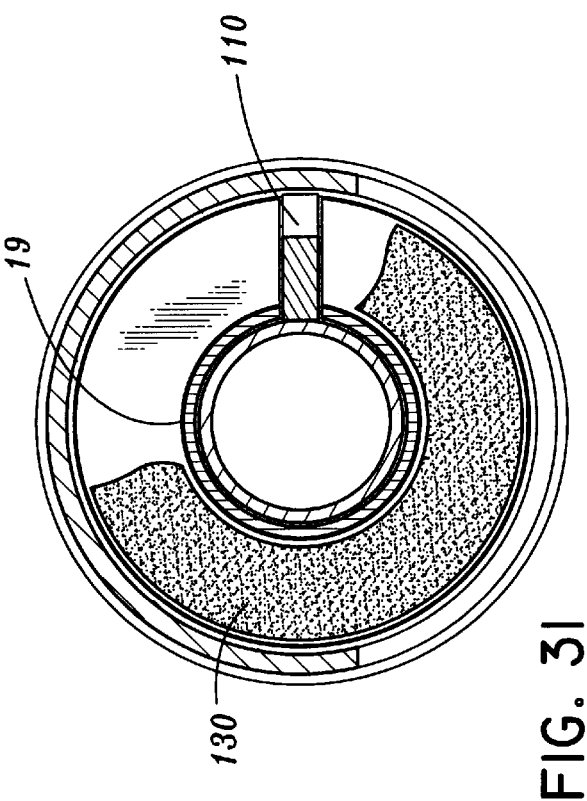
FIG. 30
FIG. 31
FIG. 29

BIOPSY APPARATUS AND METHOD

CROSS REFERENCE TO RELATED APPLICATIONS

This application claims priority to U.S. Provisional Application Ser. No. 60/059,547 filed Sep. 19, 1997 by Bryan et al., the entire contents of which are hereby incorporated by reference.

BACKGROUND

1. Technical Field

This disclosure relates to an apparatus and method for the biopsy of tissue specimens and, more particularly, to a single insertion, multiple sample percutaneous biopsy apparatus and method.

2. Background of Related Art

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment tissue is obtained for histologic examination which may be done via frozen section or paraffin section. In more recent developments percutaneous techniques have been used to remove the entire mass during the initial procedure.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is preferred by medical personnel in order to arrive at a definitive diagnosis regarding the patient's condition. In most cases only part of the organ or lesion need be sampled. The portions of tissue extracted must be indicative of the organ or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

Mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

The introduction of stereotactic guided percutaneous breast biopsies offered alternatives to open surgical breast biopsy. With time, these guidance systems have become more accurate and easier to use. Biopsy guns were introduced for use in conjunction with these guidance systems. Accurate placement of the biopsy guns was important to obtain useful biopsy information because only one small core could be obtained per insertion at any one location. To sample the lesion thoroughly, many separate insertions of the instrument had to be made.

Biopsy procedures may benefit from larger tissue samples being taken, for example, tissue samples as large as 10 mm across. Many of the prior art devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow needle via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. Such devices generally contemplate advancing a hollow needle into a tissue mass and applying a vacuum force to draw a sample into the needle and hold the same therein while the tissue is extracted.

When extracting multiple samples with a single insertion of the biopsy device using suction to either draw in tissue or remove the tissue from the body, it is important that the vacuum path remain unclogged. If the vacuum path clogs, the sample removal will become difficult or impossible. This may necessitate multiple insertions of the device or reduce the sample mass per extraction.

Therefore, a continuing need exists for percutaneous biopsy apparatus and methods which can reliably extract adequate biopsy sample(s) with a single insertion of the biopsy instrument.

SUMMARY

The present disclosure describes an apparatus and method for the biopsy of tissue specimens and, more particularly, to a single insertion multiple sample percutaneous biopsy apparatus and method. A tip at a distal end of a vacuum support tube is introduced into a tissue mass. The vacuum support tube is retracted exposing a basket tube bounded by a front washer and a rear washer mounted thereabout forming a tissue basket. The basket tube is supported internally by a thrust tube which provides structure to the apparatus to allow it to penetrate tissue. The thrust tube and the basket tube are in fluid communication and are provided with suction to draw tissue inward. The tissue is then severed by rotating and advancing a knife edge at the distal end of the vacuum support tube. The tissue basket is withdrawn and the tissue sample is removed by rotating the vacuum support tube. The tissue sample is sliced longitudinally, and a stripper scrapes the tissue sample from an opening in the vacuum support tube.

The surgical biopsy apparatus disclosed includes a base portion having a proximal and a distal end. Desirably, the base portion further comprises a nose support, a center support and a back support.

The apparatus further includes a first elongated tubular member having a proximal and a distal end and is removably supported in the base portion and further defines a fluid passageway. The proximal end of the first elongated member is supported at the proximal end of the base portion. The first elongated tubular member includes a tip portion disposed at its distal end and adapted to penetrate tissue and a plurality of openings formed adjacent its distal end and in fluid communication with the fluid passageway. Preferably, the distal end of the first elongated tubular member is supported at the back support of the base portion.

Most preferably, the tip has a tapered closed distal end and a stepped proximal end configured to cooperatively engage the distal end of the first elongated tubular member.

A suction junction is fixedly supported at the proximal end of the base portion and removably mounted to the proximal end of the first elongated tubular member and in fluid communication therewith.

The apparatus also includes a second elongated tubular member having a proximal and a distal end and is reciprocatingly disposed coaxially about the first elongated tubular member and is movable from a retracted position to an extended position. The distal end of the second elongated tubular member is disposed laterally adjacent to the plurality of openings of the first elongated member and supported at the proximal end of the base portion. The second elongated tubular member defines a tissue receiving portion disposed adjacent to its distal end and further defines a plurality of openings in fluid communication with the plurality of openings of the first elongated member. Preferably, the second elongated tubular member is supported at the back support of the base portion.

A third elongated tubular member is included having a proximal and an open distal end and is slidably mounted to the base portion and rotatably and reciprocatingly disposed coaxially about the first and second elongated tubular members. The third elongated tubular member includes a cutting edge formed at the open distal end and a lateral tissue discharge port. The third elongated tubular member is movable from an extended position wherein the cutting edge is disposed adjacent the tip portion of the first elongated tubular member and a retracted position wherein the lateral tissue discharge port is disposed laterally adjacent the tissue receiving portion of the second elongated tubular member. A vacuum port assembly is fixedly mounted to the proximal end of the second elongated tubular member and in fluid communication therewith. Preferably, a control member mounted to its proximal end. Most preferably, the control member has a circular configuration and defines a knurled outer peripheral surface.

In a preferred embodiment, the apparatus includes a latch plate assembly attached to the base portion between the center and back supports. The latch plate assembly includes a first latch having a cantilevered portion and a camming surface resiliently biased against the control member. The cantilevered portion releasably locks the third elongated tubular member at its distalmost position.

In another preferred embodiment, the latch plate assembly further comprises a second latch having a cantilevered portion and a camming surface resiliently biased against the vacuum port assembly. The cantilevered portion releasably locks the vacuum port assembly at its distalmost position.

In yet another preferred embodiment, the second elongated tubular member defines a fluid passageway in fluid communication with the vacuum port assembly. Preferably, the second elongated tubular member further includes a front washer and a rear washer that define the tissue receiving portion therebetween. The rear washer further defines a plurality of transverse openings spaced radially thereabout in fluid communication with the fluid passageway of the second elongated tubular member.

In one particular embodiment, a cutting element is longitudinally attached to an exterior surface of the first elongated tubular member and positioned to sever a tissue sample. Preferably, the second elongated tubular member defines a slot for receiving the cutting element.

In another embodiment, the apparatus comprises a tissue stripping member mounted to the base portion and disposed between the nose support and the center support. The tissue stripping member includes a flexible extended portion configured and dimensioned to enter the tissue discharge port of the third elongated tubular member upon alignment of the tissue discharge port with the tissue receiving portion of the second elongated tubular member. Preferably, the tissue stripping member includes a friction reducing coating formed thereon to reduce friction with body tissue coming in contact with the tissue stripping member.

A method of performing a surgical biopsy is disclosed comprising the steps of: inserting a biopsy apparatus into the tissue of a patient, the biopsy apparatus including: a first elongated tubular member defining a fluid passageway and having a tip portion at the distal end for penetrating tissue and further defining a plurality of openings formed adjacent the distal end and in fluid communication therewith, a second elongated tubular member defining a tissue receiving portion and a plurality of openings in fluid communication with the plurality of openings of the first elongated tubular member, and a third elongated tubular member having a cutting edge formed at an open distal end and defining a lateral tissue discharge port, extending the second elongated tubular member to align the plurality of openings of the first elongated tubular member and the plurality of openings of the second elongated tubular member, retracting the third elongated tubular member to expose the tissue receiving portion of the second elongated tubular member, applying suction to the fluid passageway of the first elongated tubular member in fluid communication with the plurality of openings of the first elongated tubular member and thereby in fluid communication with the plurality of openings of the second elongated tubular member to pull tissue into the tissue receiving portion, severing tissue disposed within the tissue receiving portion by extending the third elongated tubular member to adjacent the closed distal tapered end portion of the first elongated tubular member such that a cutting surface formed on the open distal end of the third elongated tubular member rotates as it passes over the tissue receiving portion, and removing the severed tissue sample from the tissue sampling site by applying suction to a fluid passageway defined in the second elongated tubular member in fluid communication with a plurality of openings defined within a rear washer of the second elongated tubular member, retracting the second elongated tubular member and thereby pulling the severed tissue sample until the tissue receiving portion is aligned with the lateral discharge port of the third elongated tubular member wherein a tissue stripping plate urges the tissue sample out of the tissue receiving portion.

BRIEF DESCRIPTION OF THE DRAWINGS

Various embodiments are described herein with reference to the drawings, wherein:

FIG. 2 is an exploded perspective view of the biopsy apparatus of FIG. 1;

FIG. 3 is a perspective view of an area of detail indicated in FIG. 2;

FIG. 4 is a perspective view of an area of detail as indicated in FIG. 2;

FIG. 8 is an exploded perspective view of a basket tube and a vacuum port;

FIG. 9 is a rotated exploded perspective view of the basket tube and the vacuum port of FIG. 8;

FIG. 11 is a cross sectional view of the biopsy apparatus of FIG. 1;

FIG. 12 is a cross-sectional view of an area of detail indicated in FIG. 11;

FIG. 13 is a cross-sectional view of an area of detail indicated in FIG. 11;

FIG. 14 is an enlarged perspective view of a tip portion of the biopsy apparatus of FIG. 1 with the cutting tube broken away;

FIG. 15 is an enlarged perspective view of a tip portion of the biopsy apparatus of FIG. 1 with the cutting tube and the basket tube broken away;

FIG. 18 is a cross sectional view of the biopsy apparatus of FIG. 1 showing the cutting tube retracted to accept a tissue sample;

FIG. 19 is a cross-sectional view of an area of detail indicated in FIG. 18;

FIG. 22 is a perspective view showing a tissue sample being sliced longitudinally;

FIG. 23 is a cross-sectional view of the biopsy apparatus of FIG. 1 showing the tissue sample ready to be removed from the cutting tube;

FIG. 24 is a cross-sectional view of an area of detail indicated in FIG. 23;

FIG. 25 is a cross-sectional view taken along section line 25—25 of FIG. 24;

FIG. 26 is a cross-sectional view showing forceps removing the tissue sample;

FIG. 27 is a cross-sectional view showing a stripping plate removing the tissue sample;

FIG. 28 is a perspective view of a biopsy apparatus having a stripping plate attached thereto;

FIG. 29 is a perspective view of a basket converter;

FIG. 30 is an enlarged perspective view of a tip portion showing a basket converter mounted therein; and FIG. 31 is a cross-sectional view taken along section lines 31—31 of FIG. 30.

DETAILED DESCRIPTION OF PREFERRED EMBODIMENTS

Figure 1:
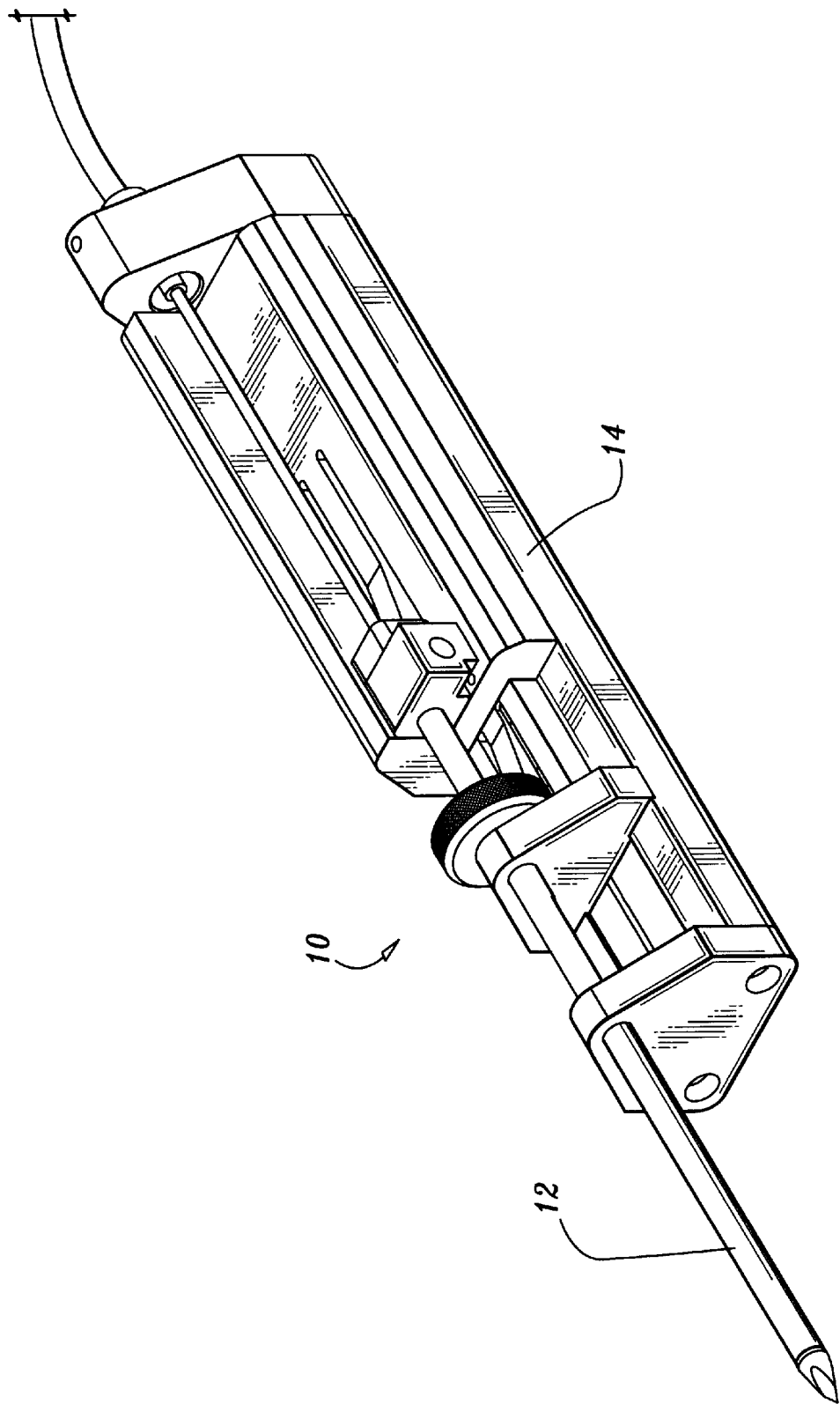
FIG. 1 is a perspective view of a biopsy apparatus.

Referring now in specific detail to the drawings, in which like reference numerals identify similar or identical elements throughout the several views, and initially to FIG. 1, a biopsy apparatus constructed in accordance with the present disclosure is shown generally as biopsy apparatus 10. Biopsy apparatus 10 includes an insertion portion 12 and a base portion 14.

Referring to FIGS. 2, 3 and 4, a tip 13 is rigidly mounted to distal end 15 of a thrust tube 16. Thrust tube 16 is disposed in a basket tube 18 which slides longitudinally along thrust tube 16. Basket tube 18 has a front washer 20 and a rear washer 22 mounted thereon. Front washer 20 and rear washer 22 are spaced a predetermined distance apart bounding a basket portion 19 of basket tube 18.

Basket portion 19 has a smaller diameter than basket tube 18. Basket portion 19, front washer 20 and rear washer 22 are dimensioned to fit within a cutting tube 24 and form a tissue basket 27 for receiving tissue therein. Basket portion 19 has a plurality of holes 114 provided therethrough in order to be able to communicate with suction provided through thrust tube 16 during operation. A vacuum port 28 attaches to a proximal end of basket tube 18 for providing an attachment to a vacuum source (not shown). A razor blade 106 is longitudinally attached to an exterior surface 108 of thrust tube 16 and extends therefrom in a radially outward direction. A suction knob 66 is shown for attaching to a proximal end of thrust tube 16.

Figure 5:
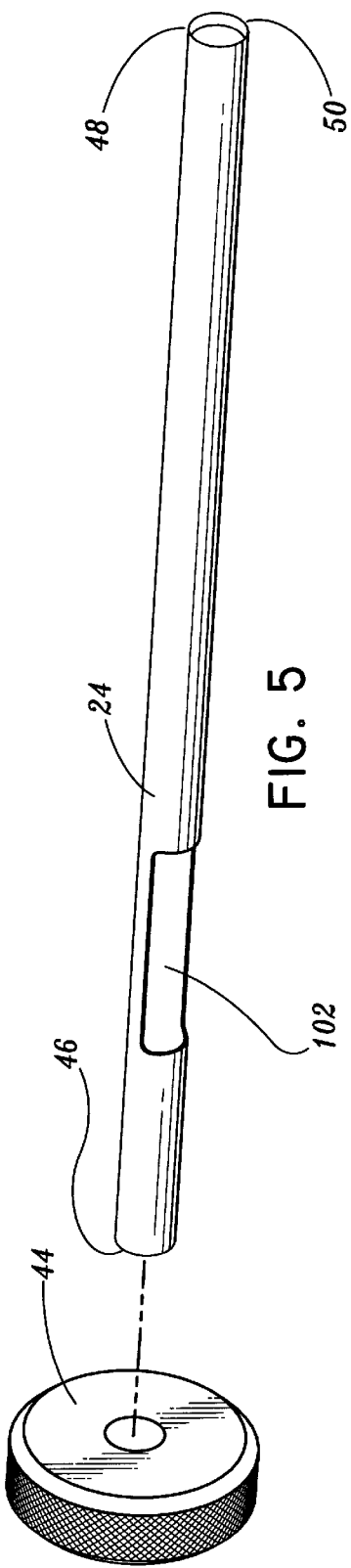
FIG. 5 is an exploded perspective view of a cutting tube.
Figure 6:
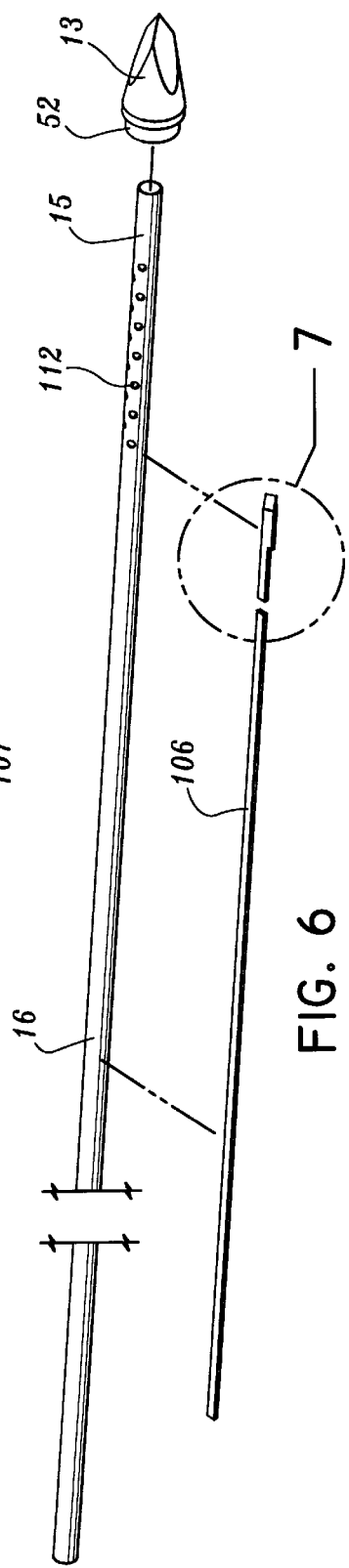
FIG. 6 is an exploded perspective view of a thrust tube and a razor blade.

Turning now to FIG. 5, a knob 44 is rigidly mounted to a proximal end 46 of cutting tube 24. Knob 44 is used to rotate cutting tube 24. The surface of knob 44 can be knurled to improve grip when rotating cutting tube 24. A distal end 48 of cutting tube 24 is stone ground to form a sharpened edge 50 thereabout. Distal end 48 receives a stepped portion 52 of tip 13 of thrust tube 16 (FIG. 6). Distal end 48 and stepped portion 52 (FIG. 6) are dimensioned to provide a shearing action therebetween. Cutting tube 24 has an opening 102 located thereon for retrieving tissue samples from therein.

Figure 7:
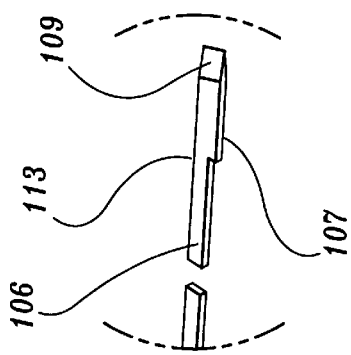
FIG. 7 is an enlarged view of the razor blade of FIG. 6.

Referring to FIGS. 6 and 7, thrust tube 16 has a plurality of holes 112 near distal end 15. Distal end 15 of thrust tube 16 is rigidly attached to tip 13. Razor blade 106 attaches to thrust tube 16 by brazing, welding or other compatible process. A leading edge 109 of razor blade 106 can be placed proximally to plurality of holes 112 in thrust tube 16 to place razor blade 106 in a position to cut a tissue sample when basket portion 19 is retracted. A tab 107 is formed on a distal end portion 113 of razor blade 106.

Referring to FIGS. 8 and 9, vacuum port 28 defines a suction port 32, a basket tube port 34 and a through hole 36 for thrust tube 16. Suction port 32, basket tube port 34 and through hole 36 fluidly communicate within vacuum port 28. Basket tube 18 has a proximal end 26 which is rigidly mounted within basket tube port 34. Basket tube 18 fluidly communicates with vacuum port 28 through a hole 29 formed on basket tube 18. Vacuum port 28 is connected to a vacuum source (not shown) by a fitting 31 which connects to suction port 32. An O-ring cap 40 of vacuum port 28 is removable to aid in assembly of basket tube 18. An O-ring 38 is supported by O-ring cap 40 which has a bore 41 therein to prevent air leakage between O-ring cap 40 and vacuum port 28. O-ring 38 is preloaded and secured by O-ring cap 40 which is attached to vacuum port 28 thereby compressing O-ring 38 therebetween.

Figure 10:
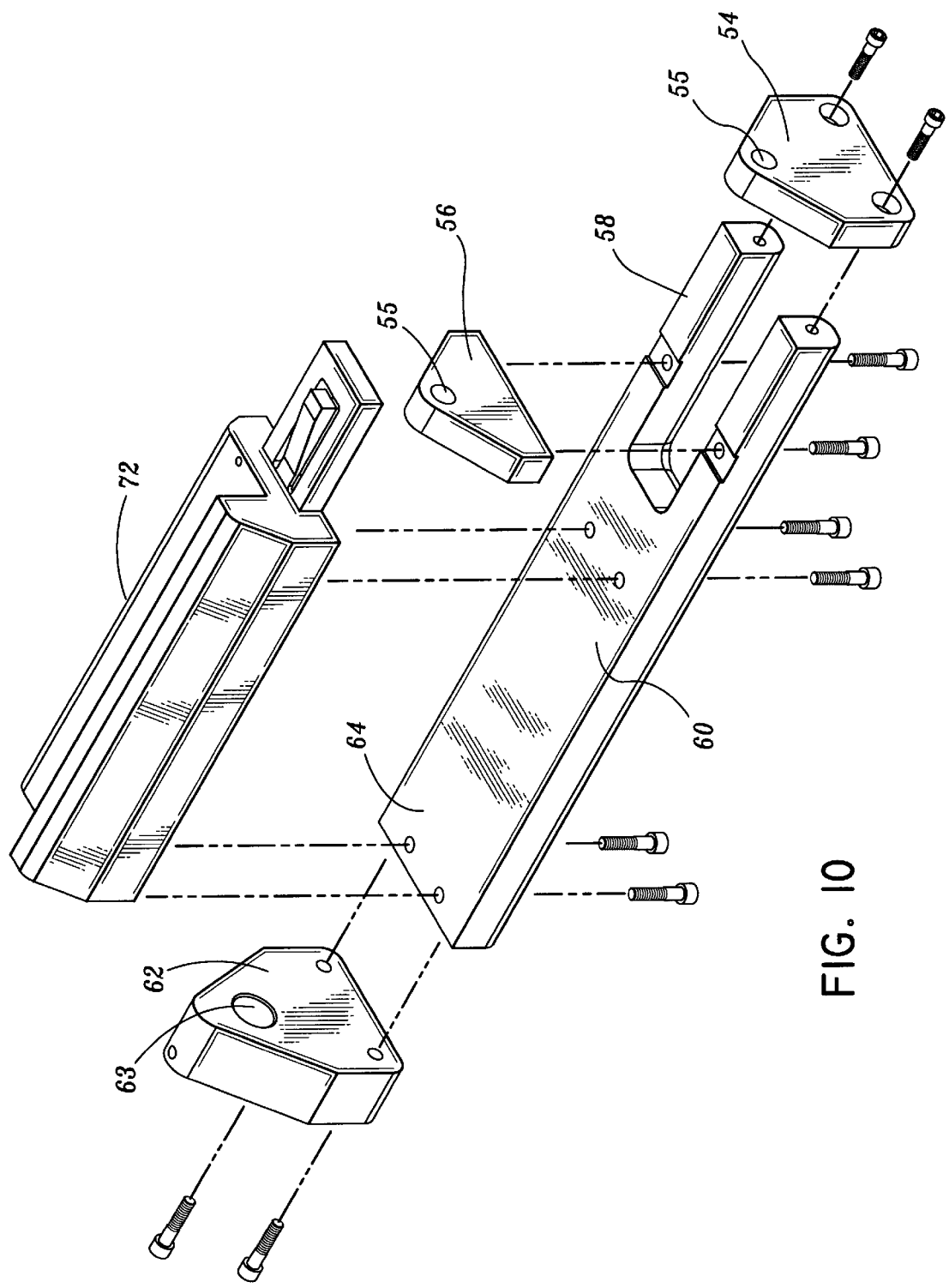
FIG. 10 is an exploded perspective view of a base with supports and a latch plate.

FIG. 10 illustrates base portion 14 of FIG. 1. Cutting tube 24 (FIG. 2) is supported by a nose support 54 and a center support 56 through bores 55. Nose support 54 and center support 56 allow axial translation and rotation of cutting tube 24. Nose support 54 is attached at a distal end 58 of a base 60 and center support 56 is spaced apart and mounted to base 60 at a predetermined distance from nose support 54. Base 60 has a back support 62 attached at a proximal end 64. Back support 62 has a bore 63 therethrough which receives suction knob 66 (FIG. 2) therein. Suction knob 66 is rigidly mounted on a proximal end 68 of thrust tube 16 (FIG. 2). A latch plate 72 is attached to base 60 between back support 62 and center support 56.

Referring to FIGS. 11 and 12, latch plate 72 has a distal end portion 74 having a first latch 76 cantilevered therefrom. First latch 76 has a camming surface 78 thereon which has a high point 80 distally disposed. Latch plate 72 has a proximal end portion 88 with a second latch 90 cantilevered therefrom. Second latch 90 has a camming surface 92 thereon which has a high point 94 distally disposed. Vacuum port 28 and knob 44 are shown in their distalmost positions. Suction knob 66 is disposed in bore 63 of back support.

Referring to FIG. 12, knob 44 (as seen in FIG. 11) in its distal most position corresponds to tissue basket portion 19 being fully enclosed within cutting tube 24. Edge 50 of cutting tube 24 receives stepped portion 52 of tip 13. Rear washer 22 is disposed within the distal end of basket tube 18. Basket tube 18, front washer 20 and rear washer 22 are dimensioned and configured to fit within cutting tube 24. An annular region 21 is formed between cutting tube 24 and basket portion 19. Thrust tube 16 is disposed within basket tube 18 such that plurality of holes 114 in basket tube 18 are substantially aligned with plurality of holes 112 in thrust tube 16 and holes 114 and holes 112 fluidly communicate with annular region 21.

Referring to FIG. 13, opening 102 in cutting tube 24 is closed by basket tube 18 when vacuum port 28 (FIG. 11) is fully advanced distally. Razor blade 106 is shown in phantom dispose on thrust tube 16.

Referring to FIGS. 14 and 15, razor blade 106 is dimensioned to fit inside cutting tube 24. Basket tube 18 has a slit 111 which allows tab 107 of razor blade 106 to fit therethrough. A longitudinal slot 110 continues through front washer 20 (in phantom), basket portion 19 and rear washer 22. Razor blade 106 prevents relative rotation between thrust tube 16 and basket tube 18. Rear washer 22 has a plurality of holes 116 therethrough for fluidly communicating between basket portion 19 and basket tube 18 when disposed within cutting tube 24.

Figure 16:
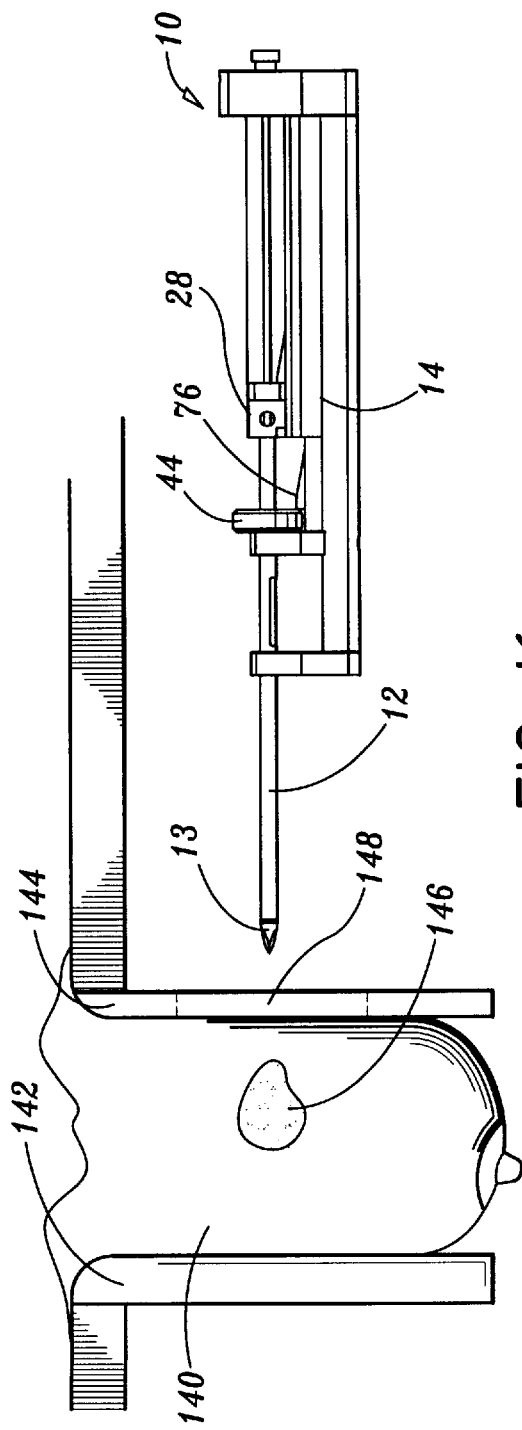
FIG. 16 is a side view of the biopsy apparatus of FIG. 1 prior to insertion into a breast.
Figure 17:
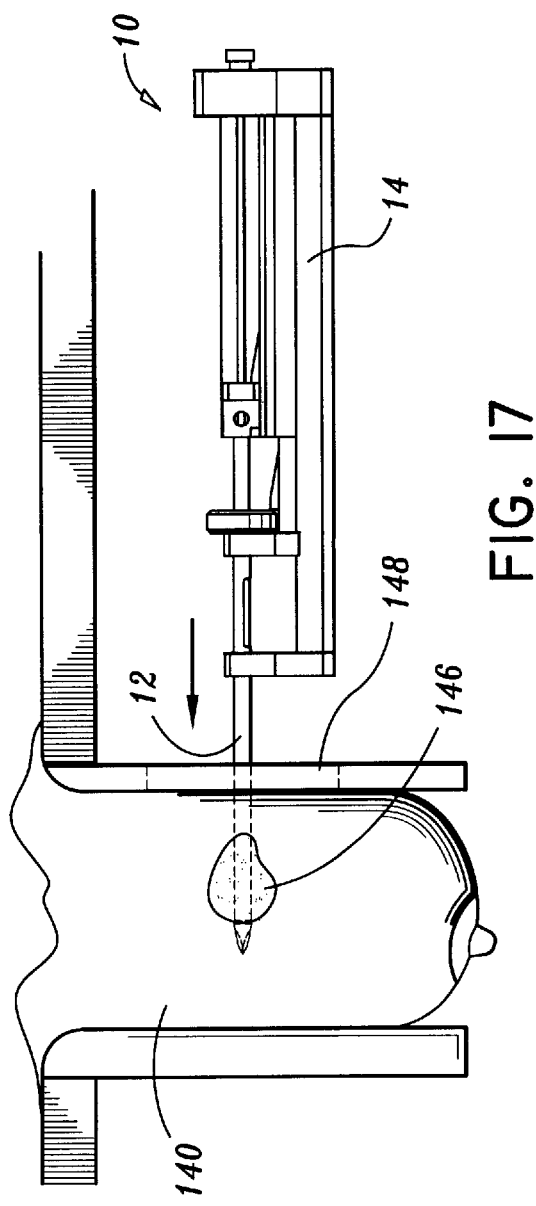
FIG. 17 is a side view of the biopsy apparatus of FIG. 1 after insertion into the breast.

Referring to FIGS. 16 and 17, during a biopsy procedure a patient's breast 140 is disposed between a movable clamp 142 and a stationary clamp 144. Movable clamp 142 is moved toward stationary clamp 144 capturing breast 140 therebetween. Upon securing breast 140 in position a guidance system (not shown) locates a target tissue mass 146 within breast 140. Assembly 10 is aimed at target tissue mass 146 such that insertion portion 12 is aligned with the direction of advancement of base portion 14. Stationary clamp 144 defines an opening 148 therethrough to allow insertion portion 12 to enter breast 140. Before insertion into breast 140, vacuum port 28 and cutting tube 24 are fully advanced distally to locate tissue basket 19 adjacent to tip 13 and to enclose basket portion 19, respectively, as shown in FIGS. 11 and 12. Knob 44 is secured by first latch 76 in the distalmost position of knob 44. A nick at the point of insertion of tip 13 is desirable for easy entry into breast 140. Tip 13 is inserted at the location of the nick into breast 140. Guidance systems are employed for determining the location of tip 13 inside the patient's body, and typically include x-rays and stereotactic devices. Insertion portion 12 is advanced distally into breast 140 until basket portion 19 is located adjacent to or within target tissue mass 146 as desired.

Referring to FIGS. 18 and 19, front washer 20 of basket portion 19 is held in contact with tip 13 inside cutting tube 24. Vacuum port 28 is in its distalmost position and secured in place by second latch 90. First latch 76 is deflected in the direction of arrow "A" by pressing down on first latch 76, thereby releasing knob 44 and allowing knob to move proximally. Cutting tube 24 is retracted by moving knob 44 proximally, thereby exposing tissue basket 19 to target tissue mass 146.

Suction is applied through thrust tube 16 which is communicated through plurality of holes 112 at distal end 15. Plurality of holes 112 at distal end 15 of thrust tube 16 communicate with plurality of holes 114 in basket portion 19. Suction draws target tissue mass 146 into tissue basket 19 circumferentially about tissue basket 19. Target tissue mass 146 is now prepared for severing.

When a predetermined period of time has elapsed suction is applied to vacuum port 28 as well. Vacuum port 28 communicates with basket tube 18 which communicates with plurality of holes 116 through rear washer 22. This draws target tissue mass 146 against rear washer 22 and secures the tissue mass thereto.

Figure 20:
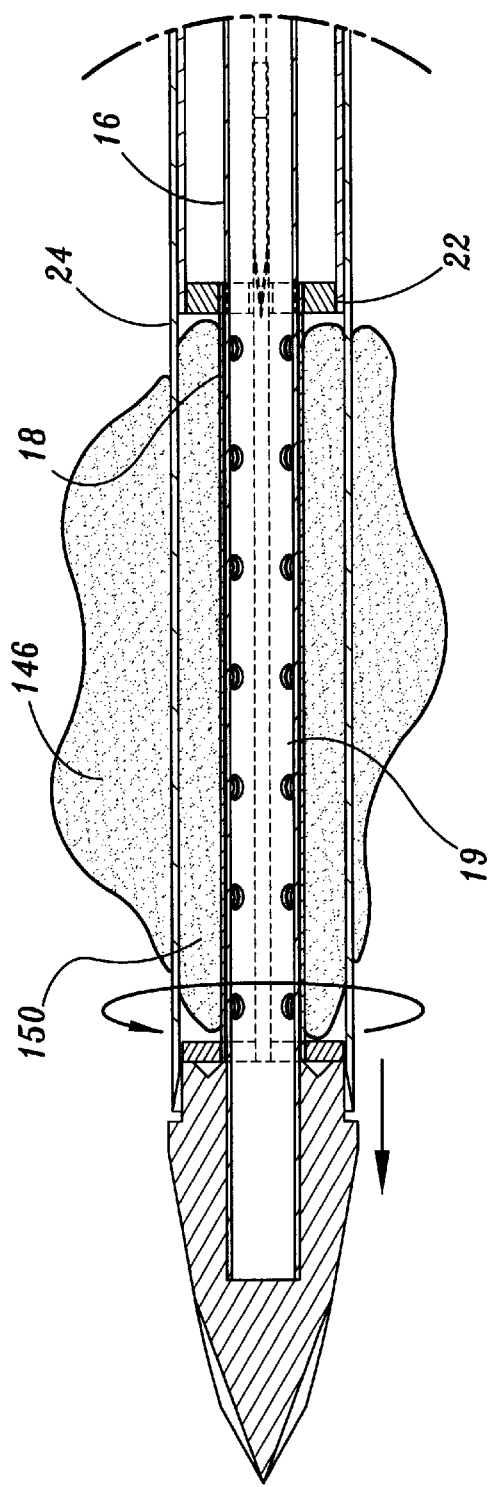
FIG. 20 is a cross-sectional view of the area of detail indicated in FIG. 18 showing the cutting tube advanced and rotated.
Figure 21:
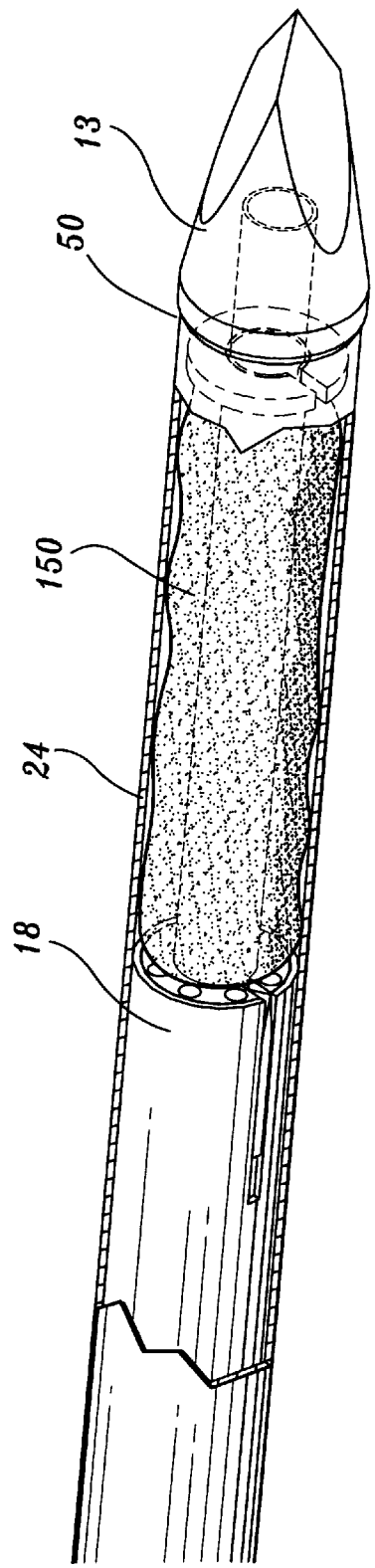
FIG. 21 is a perspective view showing a tissue sample severed and disposed in a basket portion.

Referring to FIGS. 20 and 21, knob 44 is used to translate and rotate cutting tube 24 simultaneously. Knob 44 is translated distally to allow edge 50 of cutting tube 24 to sever a tissue sample 150 from target tissue mass 146. Knob 44 is rotated and advanced distally in a simultaneous motion to sever target tissue mass 146 about tissue basket 19. Target tissue mass 146 is cut with edge 50 of cutting tube 24 to form an annular tissue sample 150. Knob 44 moves up camming surface 78 of first latch 76 as knob 44 is advanced and finally knob 44 is locked in its distalmost position by first latch 76. The distalmost position of knob 44 corresponds with edge 50 engaging stepped portion 52 of tip 13 completing the severing of tissue sample 150 and closing off tissue basket 19. As cutting tube 24 severs tissue sample 150, suction through basket tube 18 and rear washer 22 provides an opposing force against the distal motion of cutting tube 24 to allow tissue sample 150 to be severed. First latch 76 secures knob 44 and cutting tube 24 in the distalmost position. When edge 50 of cutting tube 24 has reached tip 13, tissue sample 150 is severed and may be removed from breast 140.

Referring to FIGS. 22 and 23, after tissue sample 150 is severed, suction may be removed from thrust tube 16. Second latch 90 is deflected in the direction of arrow "B" by pressing down on second latch 90, thereby releasing vacuum port 28 and allowing vacuum port 28 to be moved proximally. With suction maintained on basket tube 18 through vacuum port 28, vacuum port 28 is moved proximally thereby retracting basket tube 18 and tissue basket 19. As basket tube 18 and tissue basket 19 are retracted, razor blade 106, disposed within slot 110, slices tissue sample 150 longitudinally. Suction through plurality of holes 116 in rear washer 22 provides an opposing force to allow tissue sample 150 to be sliced.

Referring to FIGS. 24, 25 and 26, tissue sample 150 may be accessed for removal through opening 102. Razor blade 106 has provided tissue sample 150 with a longitudinal slit to allow tissue sample 150 to be peeled from basket portion 19.

During tissue sample 150 removal, tip 13 and cutting tube 24 remain adjacent to tissue mass 146. Upon removal of a first tissue sample 150, for example by forcep: tissue basket 19 may be reintroduced adjacent to tip 13 within the patient's body. Cutting tube 24 is retracted to accept more tissue mass 146 and the process as described hereinabove is repeated until enough tissue samples are collected or the targeted tissue mass 120 is removed, as necessary. A single insertion of biopsy apparatus 10 can therefore remove multiple tissue samples.

Referring to FIG. 27, a stripper plate 200 is mounted to base 60 between nose support 54 and center support 56. Opening 102 of cutting tube 24 is disposed between nose support 54 and center support 56 when knob 44 is in its distalmost position. Opening 102 corresponds to a stripping surface 204 on stripper plate 200 which also aligns with basket portion 19 such that tissue samples may be removed when basket portion 19 is rotated by turning thrust tube 16. Basket portion 19 is aligned with opening 102 and stripper plate 200 when vacuum port 28 and therefore basket tube 18 are in a proximalmost position.

Suction is removed from thrust tube 16 and vacuum port 28. Stripping plate 200 acts as a spring and enters opening 102 when tissue basket 19, with its reduced diameter, is adjacent thereto.

Referring to FIGS. 29, 30 and 31, a basket converter 130 may be introduced into basket portion 19. Basket converter 130 is a hollow cylinder defining an open longitudinal potion 132. Open longitudinal portion 132 can be a section between 10 and 130 degrees about the basket converter 130, preferably 120 degrees. Basket converter 130 snaps over basket portion 19 to reduce the exposed area of basket portion 19. This serves to concentrate tissue mass removal to a more specific location. Tissue sampling is performed as mentioned above, however, open longitudinal portion 132 must not interfere with slot 110 and razor blade 106. Open longitudinal portion 132 must therefore be positioned over slot 110 in basket portion 19. Further an outside diameter 134 of basket converter 130 must be dimensioned to fit inside cutting tube 24.

It will be understood that various modifications may be made to the embodiments disclosed herein. For example, basket converter 130 may have different size openings therein to allow for more specialized tissue sampling. Therefore, the above description should not be construed as limiting, but merely as exemplifications of preferred embodiments.

What is claimed is:

1. A surgical biopsy apparatus, comprising:

a base portion having a proximal and a distal end;

a first elongated tubular member having a proximal and a distal end and defining a fluid passageway therein, the proximal end of the first elongated member being slidably supported at the proximal end of the base portion and extending longitudinally therefrom, the first elongated tubular member further including:

a tip portion disposed at its distal end and adapted to penetrate tissue;

a plurality of openings formed adjacent its distal end and in fluid communication with the fluid passageway;

a second elongated tubular member having a proximal and a distal end and reciprocatingly disposed coaxially about the first elongated tubular member and being movable from a retracted position to an extended position wherein the distal end of the second elongated member is disposed laterally adjacent the plurality of openings of the first elongated member, the proximal end of the second elongated member being slidably supported at the proximal end of the base portion, the second elongated tubular member defining a tissue receiving portion disposed adjacent its distal end, the tissue receiving portion defining a plurality of openings in fluid communication with the plurality of openings of the first elongated member;

a third elongated tubular member having a proximal and an open distal end and slidably mounted to the base portion and rotatably and reciprocatingly disposed coaxially about the first and second members, the third elongated tubular member including:

a cutting edge formed at the open distal end; and a lateral tissue discharge port, the third elongated tubular member being movable from an extended position wherein the cutting edge is disposed adjacent the tip portion of the first elongated tubular member and a retracted position wherein the lateral tissue discharge port is disposed laterally adjacent the tissue receiving portion of the second elongated tubular member.

2. The surgical biopsy apparatus according to claim 1, further comprising a suction junction fixedly supported at the proximal end of the base portion, the suction junction removably mounted to the proximal end of the first elongated tubular member and in fluid communication therewith.

3. The surgical biopsy apparatus according to claim 1, further including a vacuum port assembly fixedly mounted to the proximal end of the second elongated tubular member and in fluid communication therewith.

4. The surgical biopsy apparatus according to claim 3, wherein the third elongated tubular member further comprises a control member mounted to its proximal end.

5. The surgical biopsy apparatus according to claim 4, wherein the control member has a circular configuration and defines a knurled outer peripheral surface.

6. The surgical biopsy apparatus according to claim 4, wherein the base portion further comprises a nose support, a center support and a back support.

7. The surgical biopsy apparatus according to claim 6, further including a latch plate assembly attached to the base portion between the center and back supports, the latch plate assembly including a first latch having a cantilevered portion and a camming surface resiliently biased against the control member, the cantilevered portion releasably locking the third elongated tubular member at its distalmost position.

8. The surgical biopsy apparatus according to claim 7, wherein the latch plate assembly further comprises a second latch having a cantilevered portion and a camming surface resiliently biased against the vacuum port assembly, the cantilevered portion releasably locking the vacuum port assembly at its distalmost position.

9. The surgical biopsy apparatus according to claim 6, wherein the distal end of the first elongated tubular member is supported at the back support of the base portion.

10. The surgical biopsy apparatus according to claim 6, wherein the second elongated tubular member is supported at the back support of the base portion.

11. The surgical biopsy apparatus according to claim 6, further comprising a tissue stripping member mounted to the base portion and disposed between the nose support and the center support, the tissue stripping member including a flexible extended portion configured and dimensioned to enter the tissue discharge port of the third elongated tubular member upon alignment of the tissue discharge port with the tissue receiving portion of the second elongated tubular member.

12. The surgical biopsy apparatus according to claim 11, wherein the tissue stripping member includes a friction reducing coating formed thereon to reduce friction with body tissue coming in contact with the tissue stripping member.

13. The surgical biopsy apparatus according to claim 3, wherein the second elongated tubular member defines a fluid passageway in fluid communication with the vacuum port assembly.

14. The surgical biopsy apparatus according to claim 14, wherein the second elongated tubular member further includes a front washer and a rear washer mounted thereon and defining the tissue receiving portion therebetween, the rear washer defining a plurality of transverse openings spaced radially thereabout in fluid communication with the fluid passageway of the second elongated tubular member.

15. The surgical biopsy apparatus according to claim 1, wherein the tip has a tapered closed distal end and a stepped proximal end configured to cooperatively engage the distal end of the first elongated tubular member.

16. The surgical biopsy apparatus according to claim 1, wherein a cutting element is longitudinally attached to an exterior surface of the first elongated tubular member, the cutting element positioned to sever a tissue sample.

17. The surgical biopsy apparatus according to claim 16, wherein the second elongated tubular member defines a slot for receiving the cutting element.

18. A surgical biopsy apparatus, comprising:
- a base portion having a proximal and a distal end, the base portion further including a nose support, a center support and a back support;
- a latch plate assembly attached to the base portion between the center and back supports, the latch plate assembly including a first latch and a second latch wherein each latch has a cantilevered portion and a camming surface;
- a first elongated tubular member having a proximal and a distal end and removably supported in the base portion and defining a fluid passageway therein, wherein the proximal end of the first elongated member is supported by the back support of the base portion, the first elongated tubular member including:
  - a tapered closed distal end portion adapted to penetrate tissue;
  - a plurality of openings formed adjacent its distal end and in fluid communication with the fluid passageway;
  - a cutting element longitudinally attached to an exterior surface of the first elongated member and extending radially outward therefrom;
- a suction junction is fixedly supported within the back support of the base portion, the suction junction removably mounted to the proximal end of the first elongated tubular member and in fluid communication therewith;
- a second elongated tubular member having a proximal and a distal end and reciprocatingly disposed coaxially about the first elongated tubular member and being movable from a retracted position to an extended position wherein the distal end of the second elongated member is disposed laterally adjacent the plurality of openings of the first elongated member, wherein the distal end of the second elongated member is supported by the back support of the base portion, the second elongated tubular member including:
  - a front washer and a rear washer mounted thereon and defining a tissue receiving portion therebetween, the rear washer defining a plurality of openings disposed radially thereabout and the tissue receiving portion defining a plurality of openings in fluid communication with the plurality of openings of the first elongated member;
- a third elongated tubular member having a proximal and an open distal end and slidably mounted in the base portion and rotatably and reciprocatingly disposed coaxially about the first and second members, the third elongated tubular member including:
  - a cutting edge formed at the open distal end;
  - a lateral tissue discharge port, the third elongated tubular member being movable from an extended position wherein the cutting edge is disposed adjacent the tapered closed distal end portion of the first elongated tubular member and a retracted position wherein the lateral tissue discharge port is disposed laterally adjacent the tissue receiving portion of the second elongated tubular member; and
- a vacuum port assembly fixedly mounted to the proximal end of the second elongated tubular member and in fluid communication therewith.

19. A method of performing a surgical biopsy comprising the steps of:
- inserting a biopsy apparatus into the tissue of a patient, the biopsy apparatus including:
  - a first elongated tubular member defining a fluid passageway therein and further defining a plurality of openings formed adjacent a distal end and in fluid communication with the fluid passageway,
  - a second elongated tubular member defining a tissue receiving portion and a plurality of openings in fluid communication with the plurality of openings of the first elongated tubular member, and
  - a third elongated tubular member having a cutting edge formed at an open distal end and defining a lateral tissue discharge port;
- extending the second elongated tubular member to align the plurality of openings of the first elongated tubular member and the plurality of openings of the second elongated tubular member;
- retracting the third elongated tubular member to expose the tissue receiving portion of the second elongated tubular member;
- applying suction to the fluid passageway of the first elongated tubular member in fluid communication with the plurality of openings of the first elongated tubular member and thereby in fluid communication with the plurality of openings of the second elongated tubular member, to pull tissue into the tissue receiving portion;
- severing tissue disposed within the tissue receiving portion by extending the third elongated tubular member to adjacent a closed distal tapered end portion of the first elongated tubular member, such that a cutting surface formed on the open distal end of the third elongated tubular member rotates as it passes over the tissue receiving portion; and
- removing the severed tissue sample from the tissue sampling site by
- applying suction to a fluid passageway defined in the second elongated tubular member in fluid communication with a plurality of openings defined within a rear washer of the second elongated tubular member, retracting the second elongated tubular member and thereby pulling the severed tissue sample until the tissue receiving portion is aligned with the lateral discharge port of the third elongated tubular member wherein a tissue stripping plate urges the tissue sample out of the tissue receiving portion.

* * * * *